United States Patent [19]

Coddington, III et al.

[11] Patent Number: 5,190,554
[45] Date of Patent: Mar. 2, 1993

[54] APPENDIX EXTRACTOR

[75] Inventors: Charles C. Coddington, III; David L. Sarrett, both of Virginia Beach, Va.

[73] Assignees: Eastern Virginia Medical School, Norfolk; Center for Innovative Technology, Herndon, both of Va.

[21] Appl. No.: 865,068

[22] Filed: Apr. 8, 1992

[51] Int. Cl.$^5$ ............................................. A61B 17/00
[52] U.S. Cl. ......................................... 606/113; 606/1; 606/108; 606/110
[58] Field of Search .......................... 604/93, 159–161, 604/171; 606/1, 108, 110, 113, 127, 128, 47–52

[56] References Cited

U.S. PATENT DOCUMENTS

| | | | |
|---|---|---|---|
| 3,903,892 | 9/1975 | Komiya | 606/46 |
| 3,942,530 | 3/1976 | Northeved | 606/46 |
| 4,134,406 | 1/1979 | Iglesias | 606/46 |
| 4,618,885 | 10/1986 | Nagasaki et al. | 606/46 |
| 4,643,187 | 2/1987 | Okada | 606/47 |
| 4,718,419 | 1/1988 | Okada | 606/47 |
| 4,905,691 | 3/1990 | Rydell | 606/48 |
| 5,026,371 | 6/1991 | Rydell et al. | 606/113 |
| 5,084,054 | 1/1992 | Bencini et al. | 606/127 |
| 5,098,440 | 3/1992 | Hillstead | 606/113 |
| 5,108,406 | 4/1992 | Lee | 606/127 |

FOREIGN PATENT DOCUMENTS

| | | | |
|---|---|---|---|
| 0227501 | 10/1910 | Fed. Rep. of Germany | 606/113 |
| 2804058 | 8/1978 | Fed. Rep. of Germany | 606/127 |
| 3522649 | 1/1986 | Fed. Rep. of Germany | 606/127 |
| 3620385 | 1/1988 | Fed. Rep. of Germany | 606/127 |

Primary Examiner—Stephen C. Pellegrino
Assistant Examiner—Glenn Dawson
Attorney, Agent, or Firm—Whitham & Marhoefer

[57] ABSTRACT

An appendix extractor includes a cannula (10) with two spaced apart guide members (12 and 14) and an appendix grasping line (16) threaded through each of the guide members (12 and 14). Finger loops (20, 28, and 30) allow for easy insertion into a hole in the patient's abdomen, movement of the appendix grasping assembly forward from the cannula (10), and enlargement and contraction of the appendix grasping region (26) of the appendix grasping line (16).

6 Claims, 3 Drawing Sheets

APPENDIX EXTRACTOR

BACKGROUND OF THE INVENTION

1. Field of the Invention

The present invention generally relates to surgical instruments used during appendectomy and, more particularly, to a specially designed instrument used when excising an appendix.

2. Description of the Prior Art

FIG. 1 is an illustration of a human appendix 1 connected to the cecum 2 of the large intestine 4. The meso appendix 6 is a thin, triangular shaped portion connected to the appendix 1 and the small intestine 8. During an appendectomy, the base of the appendix 1 and the meso appendix 6 must be cut and sutured or stapled to halt blood flowing to the excised appendix 1.

In the past, large incisions in the patient's abdomen were required to allow access to an inflamed appendix. With the advent of laparoscopic techniques which utilize a camera, appendectomies can now be performed by making smaller holes in a patient and viewing the operation on a television display. In a typical operation, small holes are made in the patient's abdomen, the abdomen is enlarged using carbon dioxide or other suitable gas, a camera is inserted into one hole to view the operation, and instruments and suturing or stapling devices are inserted into other holes for performing the operation.

Because smaller holes are being made in the patient's abdomen, the appendix is not as accessible to the surgeon. Until this invention, surgeons have been required to use forceps to remove the appendix once it is sutured or stapled. Using forceps or other make-shift instruments is not ideal because it extends the length of time of the surgery and ties up an operating room. Therefore, a need exists for a specially designed surgical instrument for extracting an appendix which makes laparoscopy a reasonable choice for surgery (e.g., if the appendix cannot be extracted quickly using laparoscopic techniques, it may be more reasonable to make a larger incision and have freer access to the appendix).

SUMMARY OF THE INVENTION

It is therefore an object of this invention to provide a specially designed surgical instrument for excising an appendix.

According to the invention, a hand held appendix extraction tool has been developed which includes a cannula having an appendix grasping loop positioned therein. The cannula is inserted into a hole made in the patients abdomen and the appendix grasping loop moved forward to extend from the cannula and is adjusted in size so that it fits over the distal tip of the appendix. Movement and adjustments to the appendix grasping loop size are easily accomplished using finger handles connected to various parts at the rear of the appendix extractor. After the appendix is firmly grasped, it is pulled within the cannula and the meso appendix and appendix base are secured by staples or suture with the appendix being excised and held inside the cannula. After excision of the appendix, the cannula can be neatly retracted out of the patient's abdomen and the holes used for the laparoscopic camera, the suturing or stapling device, and the appendix extractor are closed.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF A PREFERRED EMBODIMENT OF THE INVENTION

Figure 1:
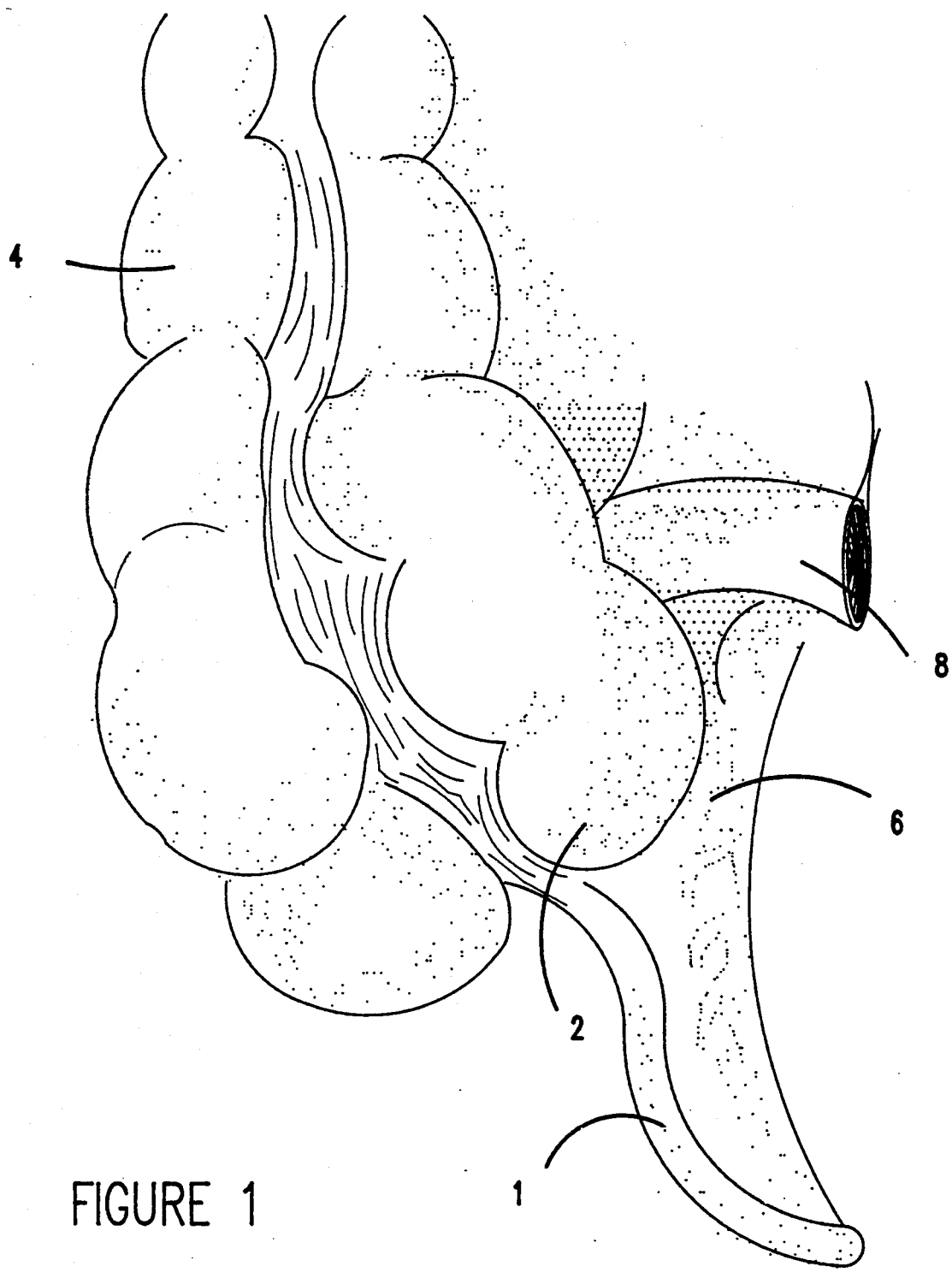
FIG. 1 is an isometric view of a human appendix.
Figure 2:
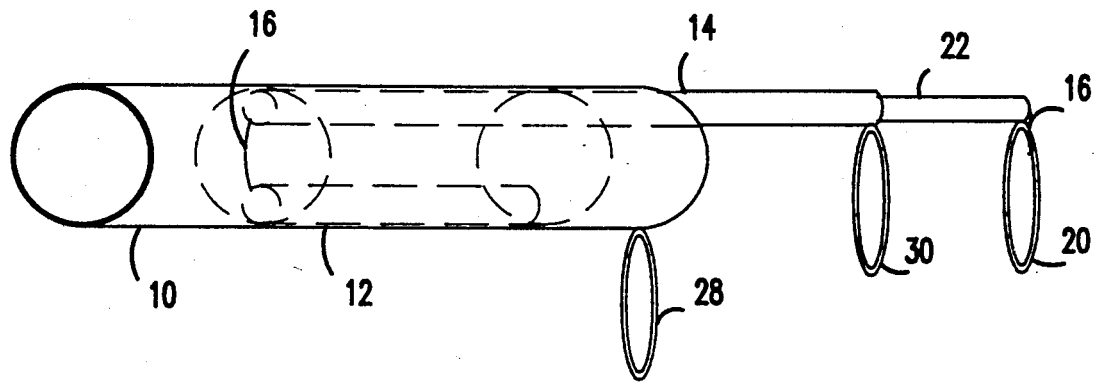
FIG. 2 is a side view of the appendix extractor of the present invention showing the appendix grasping member retracted within the outer cannula.
Figure 3:
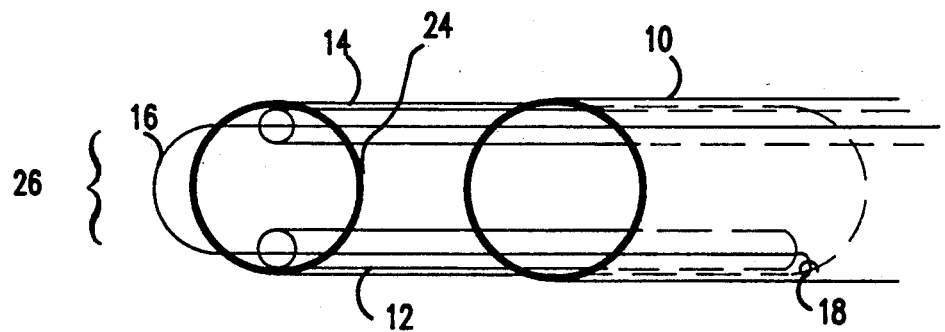
FIG. 3 is an enlarged side view of the end of the appendix extractor showing the appendix grasping member extending from the front end of the cannula.

Referring now to FIGS. 2 and 3, the appendix extractor of the present invention includes a cannula 10 having a pair of spaced apart guide members 12 and 14 positioned therein. While the guide members 12 and 14 are shown as hollow tubes, it should be understood that guide loops or other suitable guides could be used. An appendix grasping line 16 is passed through the guide members 12 and 14, and is knotted 18 at one end to secure it to guide member 12, and tied off at the other end to finger loop 20 after passing through a hollow member 22 which can slide within guide member 14. The guide members 12 and 14 are held at spaced apart locations by a tubular member 24 which can slide within the cannula 10. Other suitable devices can be used to space the guide members 12 and 14 apart, such as rings or rods or the like. The important feature is that the guide members 12 and 14 are held apart by some means so that an appendix grasping region 26 is created between the ends of the guide members 12 and 14. Finger loops 28 and 30 are used for inserting the cannula 10 into the hole in the patient's abdomen and moving the appendix grasping assembly forward so that it projects out of the front end of the cannula, respectively. In particular, moving finger loop 30 towards finger loop 28 causes the tubular member 24 with the guide members 12 and 14 to project out the forward end of the cannula 10 as is best shown in FIG. 2. This, in turn, exposes the appendix grasping region 26 of the appendix grasping line 16 so that it may be secured to the distal end of an appendix.

Figure 4:
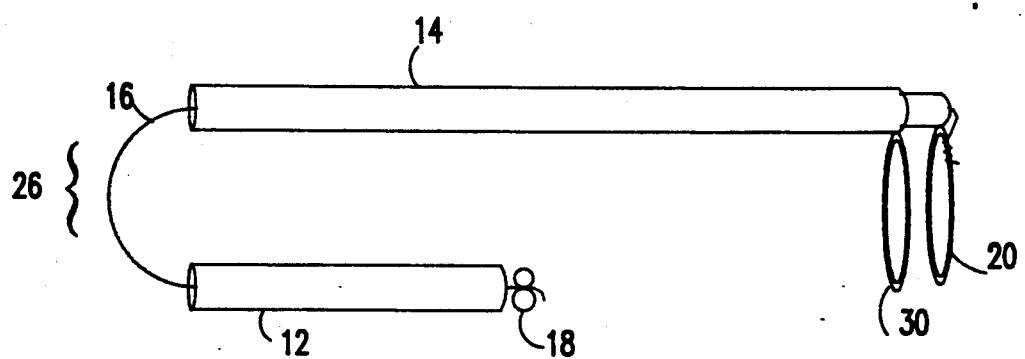
FIGS. 4 and 5 are sequential side views of the guide members and finger loops showing the means for controlling enlargement and contraction of the appendix grabbing loop.
Figure 5:
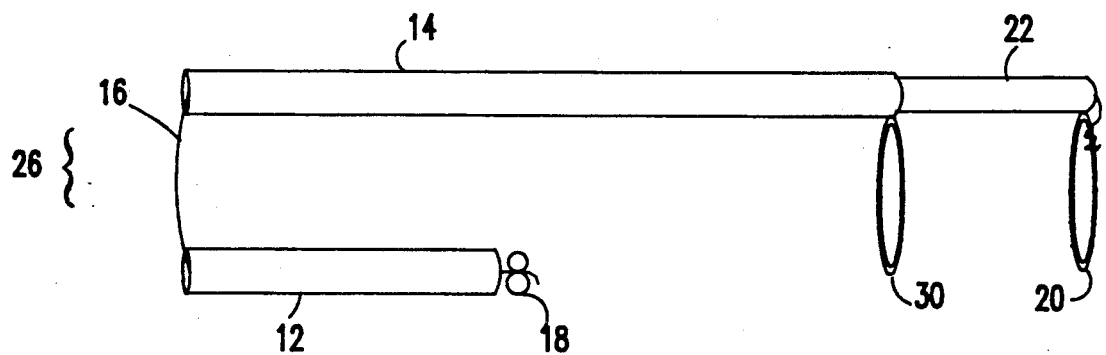

With particular reference to FIGS. 4 and 5, the appendix grasping region 26 is enlarged and contracted by moving the finger loops 20 and 30 relative to each other. When the loops 20 and 30 are moved close together, as shown in FIG. 4, slack in the appendix grasping line 16 causes the appendix grasping region 26 to enlarge (note that the appendix grasping line 16 is tied off at loop 20 and knotted 18 at the other end). Although it may not be required, the knot 18 could be secured to the guide member 12 to assure that the slack created by moving the loops together develops only at the space between the guide members 12 and 14. In addition, other securing means besides a knot 18 could be used to connect the appendix grasping line 16 to the guide member 12. The distance travelled by hollow tube 22 within the guide member 14 should be chosen such that enough of the appendix grasping line 16 is forced out the front end of the guide member 14 that the distal end of an appendix can be grasped. After the appendix is grasped, the finger loops 20 and 30 are moved apart, as is best shown in FIG. 5, which causes the appendix grasping region 26 to contract. Referring to both FIGS. 2 and 5, it can be seen that the appendix is firmly held by the appendix grasping line 16 and the tubular member 24.

During an operation, three holes would be made in a patient's abdomen. One hole would accommodate a television camera for viewing the operation. Another hole would be used by the appendix extractor described above. The last hole would be used by an suturing or stapling device such as those sold by Ethicon or U.S. Surgical. After the patient's abdomen is enlarged and the camera, appendix extractor, and stapling device are in place, the appendix grasping assembly would be moved from a retracted position in the cannula, as is shown in FIG. 2, to an extended position, as is shown in FIG. 3. The appendix grasping line 16 would be enlarged at the appendix grasping region 26, as is shown in FIG. 4, using the finger loop controls 20 and 30. After the appendix grasping line 16 is placed around the distal end of the appendix, the appendix would be grasped tightly by manipulating the finger loops 20 and 30 and pulled back within the cannula 10. The appendix is then secured and separated using the stapler by placing a row of staples across the meso appendix and the base of the appendix. Because of the different thicknesses of the meso appendix and the appendix, different staples may be required. The appendix may then be neatly pulled from the patient's abdomen by removing the appendix extractor. Because the appendix fits within the cannula 10, it will fit through the hole in the abdomen without causing it to enlarge.

The appendix extractor could be made from surgical steel, but is preferably made of a less expensive plastic material which is not harmful to the body. It is desirable to have a use-once, throw-away item because of cross-contamination problems (e.g., AIDS, hepatitis, etc.). The appendix grasping line 16 is preferably a wire, but could also be a nylon fiber or the like.

For example purposes and with reference to FIG. 2, the appendix extractor could have the following dimensions: the length of the cannula 10 is approximately 30 cm, the length of the guide member 14 which extends past the cannula 10 when the grasping assembly is retracted is approximately 8 cm, the distance between finger loops 20 and 30 may range between 20 cm and 30 cm. However, it should be understood that the size and dimensions could be greatly varied to fit the needs of the surgeon and the patient. In addition, while finger loops 20 and 30 are shown, different finger manipulated handles could be used including a rod or the like.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. An appendix extraction tool, comprising:
   a cannula sized to fit in a laparoscopic hole in a patient's abdomen having first and second ends, a first end of said cannula being insertable within a human abdomen and having an opening large enough to accommodate a human appendix;
   two spaced apart guide members positioned within said cannula;
   a first slidable member connecting said two spaced apart guide members, said first slidable member being positioned within said cannula; a means for moving said first slidable member between a first position within said cannula to a second position which may be inside or outside said first end of said cannula;
   an appendix grasping line which passes through said two spaced apart guide members, said appendix grasping line forming an appendix grasping loop between said two spaced apart guide members, said appendix grasping line being separate from said means for moving; and
   means for enlarging and contracting said appendix grasping loop which is separately operable from said means for moving including
   (i) means for securing said appendix grasping line to a first of said two spaced apart guide members, and
   (ii) a means for sliding a sufficient amount of said appendix grasping line out a first end of a second of said two spaced apart guide members for said appendix grasping loop to fit around a distal tip of said human appendix, said means for sliding including a second slidable member which can slide within said second guide member of said two spaced apart guide members relatively toward and away from said second of said two spaced apart guide members.

2. An appendix extraction tool as recited in claim 1 wherein said second slidable member is hollow and said appendix grasping line passes through said second slidable member.

3. An appendix extraction tool as recited in claim 1 wherein the first slidable member is a hollow tube.

4. An appendix extraction tool as recited in claim 1 wherein at least a portion of said two spaced apart guide members projects from said first end of said cannula when said means for moving has moved said first slidable member to said second position.

5. An appendix extraction tool as recited in claim 3 wherein said means for moving said first slidable member includes an extended portion of said second guide member of said two spaced apart guide members.

6. An appendix extraction tool as recited in claim 1 further comprising handles on said second guide member and said second slidable member.

* * * * *